United States Patent
Ok et al.

(10) Patent No.: US 8,372,996 B2
(45) Date of Patent: *Feb. 12, 2013

(54) TRANSITION METAL CATALYTIC SYSTEMS AND METHODS FOR PREPARING ETHYLENE HOMOPOLYMERS OR COPOLYMERS OF ETHYLENE AND α-OLEFINS USING THE SAME

(75) Inventors: Myungahn Ok, Daejeon (KR); Dongcheol Shin, Daejeon (KR); Jisu Jeong, Daejeon (KR); Jongsok Hahn, Daejeon (KR); Hoseong Lee, Daejeon (KR); Daeho Shin, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 1 day.

This patent is subject to a terminal disclaimer.

(21) Appl. No.: 13/063,513

(22) PCT Filed: Sep. 24, 2009

(86) PCT No.: PCT/KR2009/005442

§ 371 (c)(1),
(2), (4) Date: Mar. 11, 2011

(87) PCT Pub. No.: WO2010/038950

PCT Pub. Date: Apr. 8, 2010

(65) Prior Publication Data

US 2011/0172380 A1    Jul. 14, 2011

(30) Foreign Application Priority Data

Sep. 30, 2008 (KR) .................. 10-2008-0095869

(51) Int. Cl.
- *C08F 4/643* (2006.01)
- *C08F 4/6592* (2006.01)
- *C08F 110/02* (2006.01)
- *C08F 210/02* (2006.01)
- *B01J 31/22* (2006.01)
- *C07F 17/00* (2006.01)

(52) U.S. Cl. .......... 556/53; 502/103; 502/152; 526/160; 526/165; 526/348; 526/352; 526/943

(58) Field of Classification Search .................. 556/53; 502/152, 103; 526/160, 165, 348, 352, 943
See application file for complete search history.

(56) References Cited

U.S. PATENT DOCUMENTS

| | | | |
|---|---|---|---|
| 5,043,408 A | 8/1991 | Kakugo et al. | |
| 5,079,205 A | 1/1992 | Canich | |
| 6,329,478 B1 | 12/2001 | Katayama et al. | |
| 8,067,511 B2 * | 11/2011 | Shin et al. | 526/65 |

FOREIGN PATENT DOCUMENTS

| | | |
|---|---|---|
| EP | 0 320 762 | 6/1989 |
| EP | 0 416 815 | 3/1991 |
| EP | 0 420 436 | 4/1991 |
| EP | 0 842 939 | 5/1998 |
| JP | 61-240012 | 10/1986 |
| JP | 02-84405 | 3/1990 |
| JP | 03-2347 | 1/1991 |
| KR | 2001-0074722 | 8/2001 |

* cited by examiner

Primary Examiner — Caixia Lu

(74) Attorney, Agent, or Firm — Clark & Brody

(57) ABSTRACT

Provided are transition metal catalytic systems for preparing ethylene homopolymers or copolymers of ethylene with α-olefins. More specifically, provided are Group 4 transition metal catalysts, which is characterized in that the Group 4 transition metal catalyst comprises around the Group 4 transition metal a cyclopentadiene derivative, and at least one naphthoxide ligand(s) having aryl substituent(s) that function(s) as an electron donor and serve(s) to stabilize the catalyst system by surrounding an oxygen atom that links the ligand to the transition metal at 2-position, and there is no cross-linkage between the ligands; catalytic systems comprising such transition metal catalyst and aluminoxane cocatalyst or boron compound cocatalyst; and processes for preparing ethylene homopolymers or copolymers of ethylene with α-olefins by using the same.

10 Claims, No Drawings

TRANSITION METAL CATALYTIC SYSTEMS AND METHODS FOR PREPARING ETHYLENE HOMOPOLYMERS OR COPOLYMERS OF ETHYLENE AND α-OLEFINS USING THE SAME

TECHNICAL FIELD

The present invention relates to transition metal catalytic systems for preparing ethylene homopolymers or copolymers of ethylene with α-olefins. More specifically, it relates to Group 4 transition metal catalysts, which is characterized in that the Group 4 transition metal catalyst comprises around the Group 4 transition metal a cyclopentadiene derivative, and at least one naphthoxide ligand(s) having aryl substituent(s) that function(s) as an electron donor and serve(s) to stabilize the catalyst system by surrounding an oxygen atom that links the ligand to the transition metal at 2-position, and there is no cross-linkage between the ligands; catalytic systems comprising such transition metal catalyst and aluminoxane cocatalyst or boron compound cocatalyst; and processes for preparing ethylene homopolymers or copolymers of ethylene with α-olefins by using the same.

BACKGROUND ART

Conventionally, so-called Ziegler-Natta catalysts which consist of a titanium or vanadium compound as primary catalyst component and an alkylaluminium compound as cocatalyst component have been usually employed for preparing ethylene homopolymers or copolymers of ethylene with α-olefins. Though a Ziegler-Natta catalyst system exhibits high activity on ethylene polymerization, the catalyst system is disadvantageous in that the molecular weight distribution of the produced polymer is broad owing to irregular catalyst activation point, and it may result in irregular distribution of composition, particularly in copolymers of ethylene with α-olefin.

Recently, metallocene catalyst systems consisting of a metallocene compound of Group 4 transition metal in the Periodic Table of Elements, such as titanium, zirconium and hafnium, and methyl aluminoxane as a cocatalyst have been developed. Since the metallocene catalyst system is a homogeneous catalyst having a monomodal catalyst activation point, it can provide polyethylene having narrow molecular weight distribution and homogenous composition distribution as compared to conventional Ziegler-Natta catalyst. For example, European Patent Publication Nos. 320,762 and 3,726,325; Japanese Patent Laid-Open Nos. Sho 63-092621, Hei 02-84405 and Hei 03-2347 reported that ethylene can be polymerized with high activity by activating the metallocene compounds such as $Cp_2TiCl_2$, $Cp_2ZrCl_2$, $Cp_2ZrMeCl$, $Cp_2ZrMe_2$, ethylene$(IndH_4)_2ZrCl_2$ by using methyl aluminoxane as cocatalyst, to provide polyethylene having the molecular weight distribution (Mw/Mn) in the range from 1.5 to 2.0. However, it is difficult to obtain polymers of high molecular weight by using such a catalyst system. Particularly, when the catalyst system is applied to solution polymerization carried out at a high temperature of 140° C. or higher, the polymerizing activity abruptly decreases but β-dehydrogenation predominates, so that the system is known to be not suitable for preparing polymers having high molecular weight (weight average molecular weight, Mw) of 100,000 or more.

In the meanwhile, disclosed were so-called geo-restrictive non-metallocene type catalysts (also referred to as single activation point catalysts), wherein the transition metals are linked in the form of a ring, as catalysts for preparing high molecular weight polymers with high catalytic activity in polymerization of ethylene homopolymers or copolymerization of ethylene with α-olefin. European Patent No. 0416815 and 0420436 suggested the examples wherein amide groups are linked in the form of a ring to one cyclopentadiene ligand, while European Patent No. 0842939 showed exemplary catalysts wherein phenolic ligands (as electron donors) are linked to cyclopentadiene ligand in the form of a ring.

However, there are many difficulties to commercially utilize such catalysts since the yield of the procedure of ring formation between the ligands and the transition metal compounds is very low during the synthesis of the geo-restrictive catalyst as described above.

On the other hand, examples of non-metallocene catalysts that are not geo-restrictive can be found in U.S. Pat. No. 6,329,478 and Korean Patent Laid-Open No. 2001-0074722. It is found that the catalyst of single activation point, which employs a phosphinimine compound as a ligand, showed high ethylene conversion in the copolymerization of ethylene with α-olefin under the condition of solution polymerization at a high temperature of 140° C. or more. U.S. Pat. No. 5,079,205 discloses the examples of catalysts containing bisphenoxide ligand, and U.S. Pat. No. 5,043,408 those containing bisphenoxide ligand of chelate type. However those catalysts have so little activity that can be hardly employed for industrial preparation of ethylene homopolymers or ethylene copolymers with α-olefin, which is carried out at a high temperature.

DISCLOSURE

Technical Problem

In order to overcome the problems of conventional techniques, the present inventors carried out extensive studies, and found that non-crosslinked type catalysts, which comprises a cyclopentadiene derivative, and at least one naphthoxide ligand(s) having aryl substituent(s) that function(s) as an electron donor and serve(s) to stabilize the catalyst system by surrounding an oxygen atom that links the ligand to the transition metal at 2-position, exhibits excellent catalytic activity. Based on the discovery, the inventors developed catalysts for preparing high molecular weight ethylene homopolymers or copolymers of ethylene with α-olefin with high activity during the process of polymerization at a temperature of 60° C. or more, and completed the present invention.

Thus, an object of the invention is to provide transition metal compounds which are useful as catalysts for preparing ethylene homopolymers or copolymers of ethylene with α-olefin, catalyst compositions comprising the same, and ethylene homopolymers or copolymers of ethylene with α-olefin which were prepared by using the compound or the catalyst composition.

Another object of the invention is to provide a process for polymerization wherein a catalyst of single activation point with high activity is employed in olefin polymerization, which allows economic preparation of ethylene homopolymers or copolymers of ethylene with α-olefin from the aspect of commercialization.

Technical Solution

To achieve the objects of the present invention, one aspect of the present invention relates to Group 4 transition metal catalysts (as represented by Chemical Formula (1)), which is characterized in that the Group 4 transition metal catalyst comprises around the Group 4 transition metal a cyclopentadiene derivative, and at least one naphthoxide ligand(s) having aryl substituent(s) that function(s) as an electron donor and serve(s) to stabilize the catalyst system by surrounding an oxygen atom that links the ligand to the transition metal at 2-position, and there is no crossplinkage between the ligands; catalytic systems comprising such transition metal catalyst and aluminoxane cocatalyst or boron compound cocatalyst; and processes for preparing ethylene homopolymers or copolymers of ethylene with α-olefins.

[Chemical Formula 1]

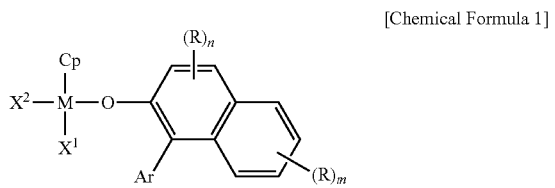

In the formula, M represents transition metal from Group 4 in the Periodic Table of Elements;

Cp represents cyclopentadienyl ring which is $\eta^5$-linkable to M, or a fused ring containing a cyclopentadienyl ring, in which the cyclopentadienyl ring or the fused ring containing a cyclopentadienyl ring may be further substituted by (C1-C20)alkyl, (C6-C30)aryl, (C2-C20)alkenyl or (C6-C30)ar(C1-C20)alkyl;

Ar represents (C6-C30)aryl, but Ar is not fluorenyl;

$X^1$ and $X^2$ are independently selected from a group consisting of halogen atoms, (C1-C20)alkyl, (C3-C20)cycloalkyl, (C6-C13)aryl, (C1-C10)alkyl(C6-C13)aryl, (C6-C30)ar(C1-C20)alkyl, (C1-C20)alkoxy, (C3-C20)alkylsiloxy, (C1-C20)alkylamino, (C6-C30)arylamino, (C1-C20)alkylphosphine, (C6-C30)arylphosphine, (C1-C20)alkylmercapto and (C6-C30)arylmercapto;

m is an integer selected from 0 to 4, n is an integer from 0 to 2;

R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy; and the alkyl, cycloalkyl, alkylaryl, aralkyl, alkoxy, alkylsiloxy, alkylamino, arylamino, alkylphosphine, arylphosphine, alkylmercapto, arylmercapto of $X^1$ and $X^2$; the alkyl, cycloalkyl, aryl, alkylaryl, aralkyl, alkoxy of R; and the aryl of Ar may be further substituted by one or more substituent(s) selected from a group consisting of (C1-C10)alkyl, (C3-C10)cycloalkyl, (C6-C13)aryl, (C1-C10)alkyl(C6-C13)aryl, (C6-C13)ar(C1-C10)alkyl and (C1-C10)alkoxy, or each of them may be linked to an adjacent substituent via (C3-C12)alkylene or (C3-C12)alkenylene with or without a fused ring to form an alicyclic ring, or a monocyclic or polycyclic aromatic ring.

Another aspect of the invention to achieve the objects described above relates to catalyst composition comprising such transition metal catalyst and aluminoxane cocatalyst or boron compound cocatalyst.

Still another aspect of the invention to achieve the objects relates to processes for preparing ethylene homopolymers or copolymers of ethylene with α-olefins using the transition metal compound or the catalyst composition.

Now, the present invention is described in more detail.

The transition metal (M) of Group 4 in the Periodic Table of Elements in Chemical Formula (1) preferably represents titanium, zirconium or hafnium.

Cp represents a cyclopentadienyl ring which is $\eta^5$-linkable to the core metal, a cyclopentadiene ring with substituent(s), or a fused ring containing a cyclopentadienyl ring, such as indenyl or fluorenyl, with or without substituent(s). More specifically, examples of Cp include cyclopentadienyl, methyl cyclopentadienyl, dimethylcyclopentadienyl, tetramethylcyclopentadienyl, pentamethylcyclopentadienyl, butylcyclopentadienyl, sec-butylcyclopentadienyl, tert-butylmethylcyclopentadienyl, trimethylsilylcyclopentadienyl, indenyl, methylindenyl, dimethylindenyl, ethylindenyl, isopropylindenyl, fluorenyl, methylfluorenyl, dimethylfluorenyl, ethylfluorenyl, isopropylfluorenyl, and so on.

The Ar substituent on the ligand may be phenyl, naphthyl, anthracenyl, or the like. Phenyl or naphthyl is preferable.

$X^1$ and $X^2$ independently represent halogen atom, (C1-C20)alkyl, (C3-C20)cycloalkyl, (C6-C13)aryl, (C1-C10)alkyl(C6-C13)aryl, (C6-C30)ar(C1-C20)alkyl, (C1-C20)alkoxy, (C3-C20)alkylsiloxy, (C1-C20)alkylamino, (C6-C30)arylamino, (C1-C20)alkylphosphine, (C6-C30)arylphosphine, (C1-C20)alkylmercapto or (C6-C30)arylmercapto;

wherein examples of halogen atom include fluorine, chlorine, bromine and iodine atoms;

examples of (C1-C20)alkyl (which is not a cyclopentadiene derivative) include methyl, ethyl, n-propyl, isopropyl, n-butyl, sec-butyl, tert-butyl, n-pentyl, neopentyl, amyl, n-hexyl, n-octyl, n-decyl, n-dodecyl, n-pentadecyl and n-eicosyl; among them methyl, ethyl, isopropyl, tert-butyl or amyl being preferable;

examples of (C3-C20)cycloalkyl include cyclopropane, cyclobutyl, cyclopentyl, cyclohexyl, cycloheptyl or adamantyl;

examples of (C6-C13)aryl or (C1-C10)alkyl(C6-C13)aryl include phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, biphenyl and naphthyl; among them phenyl, naphthyl, biphenyl, 2-isopropylphenyl, 3,5-xylyl or 2,4,6-trimethylphenyl being preferable;

examples of (C6-C30)ar(C1-C20)alkyl include benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl)methyl, (tert-butylphenyl)methyl, (n-pentylphenyl)methyl, (neopentylphenyl)methyl, (n-hexylphenyl)methyl, (n-octylphenyl)methyl, (n-decylphenyl)methyl, (n-decylphenyl)methyl, (n-tetradecylphenyl)methyl, naphthylmethyl and anthracenylmethyl; among them, benzyl group being preferable;

examples of (C1-C20)alkoxy include methoxy, ethoxy, n-propoxy, isopropoxy, n-butoxy, sec-butoxy, tert-butoxy, n-pentoxy, neopentoxy, n-hexoxy, n-octoxy, n-dodecoxy, n-pentadecoxy and n-eicocoxy; among them, methoxy, ethoxy, isopropoxy or tert-butoxy being preferable;

examples of (C3-C20)alkylsiloxy include trimethylsiloxy, triethylsiloxy, tri-n-propylsiloxy, triisopropylsiloxy, tri-n-butylsiloxy, tri-sec-butylsiloxy, tri-tert-butylsiloxy, tri-isobutylsiloxy, tert-butyldimethylsiloxy, tri-n-pentylsiloxy, tri-n-hexylsiloxy and tricyclohexylsiloxy, among them trimethylsiloxy or tert-butyldimethylsiloxy being preferable;

examples of amino groups having (C1-C20)alkyl or (C6-C30)aryl substituent(s) include dimethylamino, diethylamino, di-n-propylamino, diisopropylamino, di-n-butylamino, di-sec-butylamino, di-tert-butylamino, diisobutylamino, tert-butylisopropylamino, di-n-hexylamino, di-n-octylamino, di-n-decylamino, diphenylamino, dibenzylamino, methylethylamino, methylphenylamino, benzylhexylamino, bistrimethylsilylamino and bis-tert-butyldimethylsilylamino;

examples of phosphines having (C1-C20)alkyl or (C6-C30)aryl substituent(s) include dimethylphosphine, diethylphosphine, di-n-propylphosphine, diisopropylphosphine, di-n-butylphosphine, di-sec-butylphosphine, di-tert-butylphosphine, diisobutylphosphine, tert-butylisopropylphosphine, di-n-hexylphosphine, di-n-octylphosphine, di-n-decylphosphine, diphenylphosphine, dibenzylphosphine, methylethylphosphine, methylphenylphosphine, benzylhexylphosphine, bistrimethylsilylphosphine and bis-tert-butyldimethylsilylphosphine; among them, dimethylphosphine, diethylphosphine or diphenylphosphine being preferable;

examples of mercapto groups having (C1-C20)alkyl substituent(s) include methylmercaptane, ethylmercaptane, propylmercaptane, isopropylmercaptane, 1-butylmercaptane and isopentylmercaptane; among them, ethylmercaptane or isopropylmercaptane being preferable.

Group R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy. When m is 2 or more, or n is 2 or more, R may independently contain the same or different substituent(s).

When m is 0 or n is 0, there is no substituent but hydrogen. When m is 1 or more, or n is 1 or more, R independently represents linear or branched (C1-C10)alkyl including methyl, ethyl, n-propyl, isopropyl, n-butyl, sec-butyl, tert-butyl, n-pentyl, neopentyl, tert-amyl, n-hexyl, n-octyl, tert-octyl, preferably methyl, ethyl, n-propyl, isopropyl, n-butyl, tert-butyl or tert-octyl; (C3-C10)cycloalkyl such as cyclohexyl; (C6-C13)aryl or (C1-C10)alkyl(C6-C13)aryl including phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, biphenyl or naphthyl, preferably phenyl, naphthyl, biphenyl, 2-isopropylphenyl, 3,5-xylyl or 2,4,6-trimethylphenyl; (C6-C13)ar(C1-C10)alkyl including benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl) methyl, (tert-butylphenyl)methyl, (n-pentylphenyl)methyl, (neopentylphenyl)methyl, (n-hexylphenyl)methyl and (n-octylphenyl)methyl, preferably benzyl; (C1-C10)ar(C1-C10) alkyl including benzyl, (2-methylphenyl)methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl)methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl) methyl, (tert-butylphenyl)methyl, (n-pentylphenyl)methyl, (neopentylphenyl)methyl, (n-hexylphenyl)methyl and (n-octylphenyl)methyl, preferably benzyl, triphenylmethyl; or (C1-C10)alkoxy including methoxy, ethoxy, n-propoxy, isopropoxy, n-butoxy, sec-butoxy, tert-butoxy, n-pentoxy, neopentoxy, n-hexoxy, n-octoxy, preferably methoxy or ethoxy.

The alkyl, cycloalkyl, alkylaryl, aralkyl, alkoxy, alkylsiloxy, alkylamino, arylamino, alkylphosphine, arylphosphine, alkylmercapto, arylmercapto of $X^1$ and $X^2$; the alkyl, cycloalkyl, aryl, alkylaryl, aralkyl, alkoxy of R; and the aryl of Ar may be further substituted by one or more substituent(s) selected from (C1-C10) linear or branched alkyl including methyl, ethyl, n-propyl, isopropyl, n-butyl, sec-butyl, tert-butyl, n-pentyl, neopentyl, tert-amyl, n-hexyl, n-octyl, tert-octyl, preferably methyl, ethyl, n-propyl, isopropyl, n-butyl, tert-butyl and tert-octyl; (C3-C10)cycloalkyl such as cyclohexyl; (C6-C13)aryl or (C1-C10)alkyl(C6-C13)aryl including phenyl, 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, biphenyl or naphthyl, preferably phenyl, naphthyl, biphenyl, 2-isopropylphenyl, 3,5-xylyl or 2,4,6-trimethylphenyl; (C6-C13)ar(C1-C10)alkyl including benzyl, (2-methylphenyl) methyl, (3-methylphenyl)methyl, (4-methylphenyl)methyl, (2,3-dimethylphenyl)methyl, (2,4-dimethylphenyl)methyl, (2,5-dimethylphenyl)methyl, (2,6-dimethylphenyl)methyl, (3,4-dimethylphenyl)methyl, (4,6-dimethylphenyl)methyl, (2,3,4-trimethylphenyl)methyl, (2,3,5-trimethylphenyl)methyl, (2,3,6-trimethylphenyl)methyl, (3,4,5-trimethylphenyl) methyl, (2,4,6-trimethylphenyl)methyl, (2,3,4,5-tetramethylphenyl)methyl, (2,3,4,6-tetramethylphenyl)methyl, (2,3,5,6-tetramethylphenyl)methyl, (pentamethylphenyl)methyl, (ethylphenyl)methyl, (n-propylphenyl)methyl, (isopropylphenyl)methyl, (n-butylphenyl)methyl, (sec-butylphenyl) methyl, (tert-butylphenyl)methyl, (n-pentylphenyl)methyl, (neopentylphenyl)methyl, (n-hexylphenyl)methyl and (n-octylphenyl)methyl, preferably benzyl; and (C1-C10)alkoxy including methoxy, ethoxy, n-propoxy, isopropoxy, n-butoxy, sec-butoxy, tert-butoxy, n-pentoxy, neopentoxy, n-hexoxy, n-octoxy, preferably methoxy or ethoxy.

Examples of (C3-C12)alkylene for linkage of each substituent group to an adjacent substituent in order to form a ring with or without a fused ring include propylene, α-butylene, isobutylene, 1-pentylene, hexylene, octylene, decylene, dodecylene and pentadecylene, preferably propylene or α-butylene; and examples of (C3-C12)alkenylene include propenylene, butenylene, n-pentenylene, neopentenylene, pentenylene, hexenylene, octenylene, decenylene, dodecenylene and pentadecenylene, preferably ethenylene and isopropenylene.

Specifically, the present invention provides transition metal compounds selected from those represented by one of the following Chemical Formulas:

[Chemical Formula 1-1]

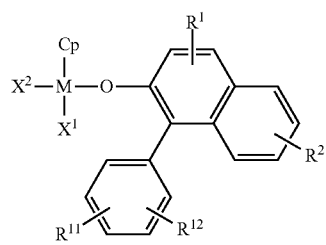

[Chemical Formula 1-2]

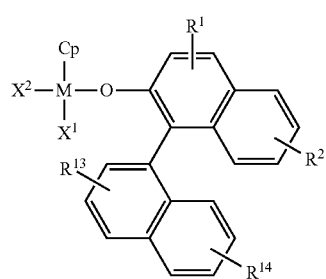

[Chemical Formula 1-3]

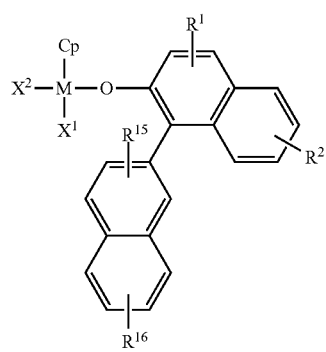

wherein, M is selected from a group consisting of titanium, zirconium and hafnium;

Cp represents cyclopentadienyl or pentamethylcyclopentadienyl;

$X^1$ and $X^2$ are independently selected from a group consisting of chloride, methyl, methoxy, isopropoxy, benzyl and dimethylamino; and $R^1$, $R^2$ and $R^{11}$ through $R^{16}$ may be independently selected from a group consisting of hydrogen atom, (C1-C10)alkyl, (C3-C10)cycloalkyl, (C6-C13)aryl, (C1-C10)alkyl(C6-C13)aryl, (C6-C13)aryl(C1-C10)alkyl and (C1-C10)alkoxy.

The (C1-C10)alkyl, (C3-C10)cycloalkyl, (C6-C13)aryl, (C1-C10)alkyl(C6-C13)aryl, (C6-C13)aryl(C1-C10)alkyl and (C1-C10)alkoxy may be selected from those exemplary groups described above.

More specifically, the transition metal compounds are characterized by being represented by one of the following Chemical Formulas:

1-1-1

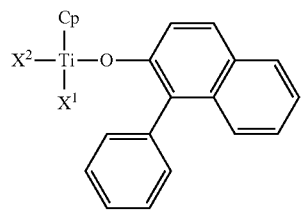

1-1-2

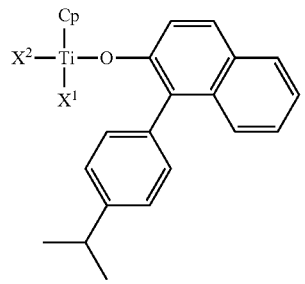

1-1-3

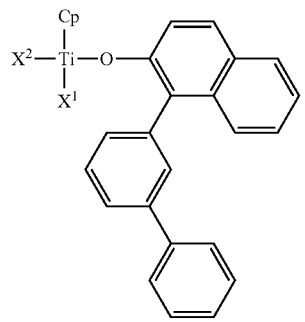

1-2-1

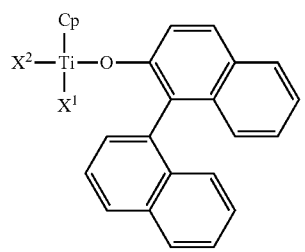

1-2-2

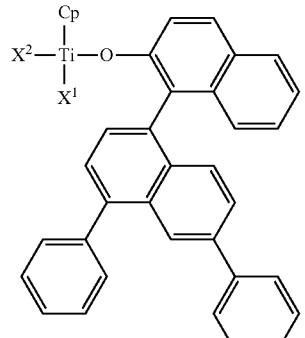

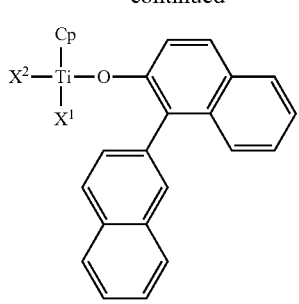

(1-3-1)

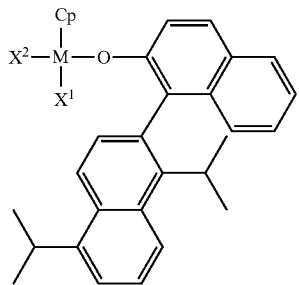

(1-3-2)

wherein, Cp represents cyclopentadienyl or pentamethylcyclopentadienyl; and $X^1$ and $X^2$ are independently selected from a group consisting of chloride, methyl, methoxy, isopropoxy, benzyl and dimethylamino.

In the meanwhile, in order to provide active catalyst component to be used for preparing ethylene homopolymer or copolymer of ethylene with α-olefin, the transition metal compound represented by Chemical Formula (1) may be employed preferably with aluminoxane compound or boron compound, or a mixture thereof as cocatalyst, which can extract X ligand from the transition metal complex to cationize the core metal and act as a counterion (that is, an anion) having weak bond strength. The compositions comprising the transition metal compound and cocatalyst as described above fall under the scope of the present invention.

The boron compounds being usable as cocatalyst according to the present invention are disclosed in U.S. Pat. No. 5,198,401, and may be selected from the compounds represented by one of Chemical Formulas (2) to (4):

   [Chemical Formula 2]

   [Chemical Formula 3]

   [Chemical Formula 4]

Wherein, B represents boron atom; $R^{21}$ represents phenyl, which may be further substituted by three to five substituent(s) selected from fluorine, (C1-C20)alkyl with or without fluorine substituent(s) and (C1-C20)alkoxy with or without fluorine substituent(s); $R^{22}$ represents (C5-C7)aromatic radical or (C1-C20)alkyl(C6-C20)aryl radical, (C6-C30)aryl(C1-C20)alkyl radical such as triphenylmethyl radical; Z represents nitrogen or phosphorus atom; $R^9$ represents (C1-C20)alkyl radical, or anilinium radical having two (C1-C10)alkyl substituent(s) with nitrogen atom; and p is an integer of 2 or 3.

Preferable examples of the boron-containing cocatalyst include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane, phenylbis(pentafluorophenyl)borane, tetrakis (pentafluorophenyl)borate, tetrakis(2,3,5,6-tetrafluorophenyl)borate, tetrakis(2,3,4,5-tetrafluorophenyl) borate, tetrakis(3,4,5-tetrafluorophenyl)borate, tetrakis(2,2,4-trifluorophenyl)borate, phenylbis(pentafluorophenyl) borate and tetrakis(3,5-bistrifluoromethylphenyl)borate. Certain compounded examples thereof include ferrocenium tetrakis(pentafluorophenyl)borate, 1,1'-dimethylferrocenium tetrakis(pentafluorophenyl)borate, silver tetrakis(pentafluorophenyl)borate, triphenylmethyl tetrakis(pentafluorophenyl)borate, triphenylmethyl tetrakis(3,5-bistrifluoromethylphenyl)borate, triethylammonium tetrakis (pentafluorophenyl)borate, tripropylammonium tetrakis (pentafluorophenyl)borate, tri(n-butyl)ammonium tetrakis (pentafluorophenyl)borate, tri(n-butyl)ammonium tetrakis(3,5-bistrifluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate and tri(dimethylphenyl)phosphonium tetrakis(pentafluorophenyl)borate. Among them, preferable are N,N-dimethylanilinium tetrakispentafluorophenylborate, triphenylmethylinium tetrakispentafluorophenylborate and trispentafluoroborane.

The aluminium compounds being usable for the present invention include aluminoxane compounds represented by Chemical Formula (5) or (6), organic aluminum compounds represented by Chemical Formula (7), or organic aluminum hydrocarbyloxide compounds represented by Chemical Formula (8) or (9):

   [Chemical Formula 5]

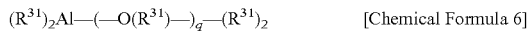   [Chemical Formula 6]

   [Chemical Formula 7]

   [Chemical Formula 8]

   [Chemical Formula 9]

Wherein, $R^{31}$ represents (C1-C20)alkyl, preferably methyl or isobutyl; l and q are independently integers from 5 to 20; $R^{32}$ and $R^{33}$ independently represents (C1-C20)alkyl; E represents hydrogen or halogen atom; r is an integer from 1 to 3; and $R^{34}$ may be selected from (C1-C20)alkyl and (C6-C30) aryl.

Specific examples of the aluminum compounds include aluminoxane compounds such as methylaluminoxane, modified methylaluminoxane, tetraisobutylaluminoxane; organic aluminum compounds such as trialkylaluminum including trimethylaluminum, triethylaluminum, tripropylaluminum, triisobutylaluminum and trihexylaluminum; dialkylaluminum chloride including dimethylaluminum chloride, diethylaluminum chloride, dipropylaluminum chloride, diisobutylaluminum chloride and dihexylaluminum chloride; alkylaluminum dichloride including methylaluminum dichloride, ethylaluminum dichloride, propylaluminum dichloride, isobutylaluminum dichloride and hexylaluminum dichloride; and dialkylaluminum hydride including dimethylaluminum hydride, diethylaluminum hydride, dipropylaluminum hydride, diisobutylaluminum hydride and dihexylaluminum hydride. Among them, preferable is trialkylaluminum, more preferable is triethylaluminum and triisobutylaluminum.

In the transition metal catalyst composition containing cocatalyst of the present invention for preparing ethylene homopolymers or copolymers of ethylene with α-olefin, ratio of the transition metal compound to the cocatalyst preferably ranges 1:0.1~100:10~1,000, more preferably 1:0.5~5:10~500 on the basis of the molar ratio of core metal: boron atom:aluminum atom.

According to another aspect of the present invention, the process for preparing ethylene polymers by using the transition metal catalyst composition is carried out by contacting the transition metal catalyst, cocatalyst and ethylene, and vinylic comonomer, if desired, in the presence of appropriate organic solvent. The transition metal catalyst and the cocatalyst component may be separately incorporated to the reactor, or those components may be previously mixed and charged to the reactor. The mixing conditions such as the order of incorporation, temperature or concentration are not particularly restricted.

Preferable organic solvents to be employed for the process for preparation include (C3-C20)hydrocarbon, specifically, butane, isobutene, pentane, hexane, heptane, octane, isooctane, nonane, decane, dodecane, cyclohexane, methylcyclohexane, benzene, toluene and xylene.

More specifically, in the preparation of ethylene homopolymer, ethylene is used alone as the monomer. Appropriate pressure for the process according to the present invention is from 1 to 1000 atm, more preferably from 10 to 150 atm. The polymerization is effectively carried out at a temperature between 60° C. and 250° C., preferably between 80° C. and 200° C.

When preparing copolymers of ethylene and α-olefin, (C3-C18) α-olefin may be used as comonomer with ethylene. The comonomer may be preferably selected from a group consisting of propylene, 1-butene, 1-pentene, 4-methyl-1-pentene, 1-hexene, 1-octene, 1-decene, 1-dodecene, 1-hexadecene and 1-octadecene, more preferably from 1-butene, 1-hexene, 1-octene and 1-decene. Preferable ethylene pressure and temperature for polymerization are the same in case of preparing ethylene homopolymers. The copolymer prepared according to the process of the invention comprises at least 50% by weight, preferably at least 60% by weight, more preferably from 60 to 99% by weight of ethylene.

As described above, the linear low density polyethylene (LLDPE) prepared by using (C4-C10) α-olefin as the comonomer has density range from 0.910 to 0.940 g/cc. It is possible to extend the process up to the range of ultra low density polyethylene (VLDPE or ULDPE) or olefin elastomer of the density of 0.910 g/cc or lower. Upon preparing the ethylene homopolymers or copolymers thereof according to the invention, hydrogen may be employed as molecular weight modifier in order to adjust the molecular weight. The weight average molecular weight (Mw) of the polymers produced is usually from 80,000 to 500,000.

Since catalyst composition proposed by the present invention exists in homogeneous state in the polymerization reactor, it can be preferably applied to solution polymerization process carried out at a temperature higher than the melting point of the corresponding polymer. However, as disclosed by U.S. Pat. No. 4,752,597, the transition metal catalyst and cocatalyst may be supported by a carrier such as porous metal oxides, so that it can be used as heterogeneous catalyst composition for slurry polymerization or a gas phase polymerization process.

Advantageous Effects

The transition metal compound according to the invention or the catalyst composition comprising the compound can be easily produced in a simple synthetic procedure with economic advantage. Due to its excellent thermal stability, the catalyst maintains high catalytic activity even at high temperature having high copolymerization reactivity with other olefins to result in polymers with high molecular weight with high yield.

BEST MODE

Hereinafter, the embodiments of the present invention will be described in detail with reference to accompanying Examples, which are not intended to restrict the scope of the invention.

Unless being stated otherwise, all experiments for synthesizing the ligands and catalysts were carried out under nitrogen atmosphere with standard Schlenk or glove-box technique, and the organic solvents were used after they had been dried via reflux over sodium metal and benzophenone, and then distilled immediately before use. $^1$H-NMR analyses of the ligands and catalysts thus synthesized were performed by using Varian Oxford 300 MHz at ambient temperature.

As the solvent for polymerization, n-heptane was used after passing through a tube filled with molecular sieve 5A and activated alumina, and being bubbled by nitrogen with high purity to sufficiently remove moisture, oxygen and other catalyst poison. The polymers thus obtained were analyzed by the methods described below.

1. Melt Flow Index (MI)

MI was measured according to ASTM D 2839.

2. Density

Density was measured by using density gradient tube, according to ASTM D 1505.

3. Analysis of Melting Temperature (Tm)

Tm was measured under $2^{nd}$ heating condition at a rate of 10° C./min in the presence of nitrogen atmosphere, by means of Dupont DSC 2910.

4. Molecular Weight and Molecular Weight Distribution

Molecular weight was measured at 135° C. at a rate of 1.0 mL/min in the presence of 1,2,3-trichlorobenzene solvent by using PL210 GPC provided with PL Mixed-BX2+preCol. Molecular weight was calibrated by using PL polystyrene standards.

5. α-Olefin Content (wt %) in Copolymer

α-Olefin content was measured by means of Bruker DRX500 NMR spectroscope at 125 MHz by using 1,2,4-trichlorobenzene/$C_6D_6$ (7/3 by weight) mixed solvent at 120° C. in the $^{13}$C-NMR mode (reference: Randal, J. C. *JMS-Rev. Macromol. Chem. Phys.* 1980, C29, 201).

PREPARATION EXAMPLE 1

Synthesis of (Dichloro)(pentamethylcyclopentadienyl)(1-phenylnaphthalen-2-yloxy)titanium (IV)

Synthesis of 1-bromo-2-methoxynaphthalene

A 500 mL three-necked round bottomed flask was charged with 2-bromonaphthalen-2-ol (30.0 g, 134.5 mmol), potassium hydroxide (KOH) (11.3 g, 201.7 mmol) and DMSO (300 mL), and the mixture was stirred under nitrogen atmosphere for 10 minutes. After cooling the reaction vessel with ice-water bath, iodomethane (28.6 g, 201.7 mmol) was slowly added dropwise thereto. When the injection of iodomethane was completed, the mixture was stirred at ambient temperature for 12 hours under nitrogen atmosphere. After stirring at 50° C. for additional 1 hour, the temperature of the mixture was cooled to ambient temperature. Water (500 mL) was added thereto, and the mixture was extracted with diethyl ether. The organic layer was washed three times with distilled water, dried over anhydrous magnesium sulfate (MgSO$_4$), and evaporated by using a rotary evaporator to remove the solvent. Purification via silica gel column chromatography (n-hexane) gave 1-bromo-2-methoxynaphthalene (22.0 g, yield: 69.0%) as white solid.

$^1$H-NMR (CDCl$_3$) δ=4.07 (s, 3H), 7.30-7.32 (d, 1H), 7.41-7.44 (t, 1H), 7.58-7.61 (t, 1H), 7.81-7.86 (m, 2H), 8.25-8.26 (d, 1H) ppm Synthesis of 2-methoxy-1-phenylnaphthalene To a flask charged with 1-bromo-2-methoxynaphthalene (20.0 g, 84.4 mmol), phenylboronic acid (11.3 g, 92.8 mmol), palladium acetate (0.10 g, 0.46 mmol), triphenylphosphine (0.85 g, 2.78 mmol) and potassium phosphate (40.9 g, 177.9 mmol), added was mixture of water (60 mL) and dimethoxyethane (120 mL), and the resultant mixture was heated under reflux for 6 hours. After cooling the mixture to ambient temperature, aqueous ammonium chloride solution (150 mL) and diethyl ether (200 mL) were injected thereto. The organic layer was isolated, and the residue was extracted with diethyl ether. The combined organic layer was dried over magnesium sulfate and evaporated to remove the volatile substances. Purification via silica gel column chromatography (n-hexane) gave 2-methoxy-1-phenylnaphthalene (13.0 g, yield: 66%) as colorless liquid.

$^1$H-NMR (CDCl$_3$) δ=3.87 (s, 3H), 7.35-7.47 (m, 6H), 7.52-7.55 (m, 3H), 7.85-7.87 (d, 1H), 7.91-7.93 (d, 1H) ppm Synthesis of 1-phenylnaphthalen-2-ol To solution of 2-methoxy-1-phenylnaphthalene (13.0 g, 55.5 mmol) in methylene chloride (300 mL), added dropwise was solution of boron tribromide (670 mL) (1M in methylene chloride) at −78° C., and the mixture reacted for three hours while slowly raising the temperature to ambient temperature. Then, mixture of ice (150 g) and diethyl ether (250 mL) was added thereto. The organic layer was isolated, and the aqueous layer was extracted with diethyl ether. The combined organic layer was dried over magnesium sulfate and evaporated to remove the volatile substances. Purification via silica gel column chromatography (eluent: mixture of hexane and methylene chloride) gave 1-phenylnaphthalen-2-ol (10.0 g, yield: 81.8%) as white solid.

$^1$H-NMR (CDCl$_3$) δ=7.29-7.31 (d, 1H), 7.35-7.39 (m, 2H), 7.53-7.56 (t, 1H), 7.61-7.64 (t, 2H), 7.83-7.86 (m, 2H) ppm Synthesis of (dichloro)(pentamethylcyclopentadienyl)(1-phenylnaphthalen-2-yloxy)titanium (IV)

To solution of 1-phenylnaphthalen-2-ol (2.0 g, 9.1 mmol) in toluene (100 mL), slowly injected was n-butyllithium (2.5 M in hexane, 3.6 mL) at −78° C., and the mixture was stirred at ambient temperature for 12 hours. After chilling the reaction mixture to −78° C., slowly added was solution of (pentamethylcyclopentadienyl)titanium(IV) trichloride (2.5 g, 16.3 mmol) in toluene (60 mL), and the reaction was carried out at ambient temperature for 12 hours. When the reaction was completed, the reaction mixture was filtered through a celite filter, and solvent was removed therefrom. Recrystallization was carried out from purified toluene and hexane at −35° C. The solid was filtered and dried under reduced pressure to obtain (dichloro)(pentamethylcyclopentadienyl)(1-phenylnaphthalen-2-yloxy)titanium(IV) (2.5 g, yield: 58.2%) as red solid.

$^1$H-NMR (C$_6$D$_6$) δ=1.87 (s, 15H), 7.27-7.32 (m, 3H), 7.43-7.46 (t, 2H), 7.58-7.60 (m, 3H), 7.70-7.73 (t, 1H), 7.92-7.94 (t, 1H) ppm Mass (APCI mode, m/z): 471.83

EXAMPLE 1

In a batch-type polymerization reactor, copolymerization of ethylene with 1-octene was carried out as described below.

In a 2000 mL stainless steel reactor, which had been sufficiently dried and purged with nitrogen, charged was cyclohexane (1140 mL) and 1-octene (60 mL). Then, 54.2 mM solution (11.1 mL) of modified methylaluminoxane-7 (modified MAO-7, 7 wt % Al Ispar solution, from Akzo Nobel) in toluene was added thereto. Then, the temperature of the reactor was raised to 140° C., and (dichloro)(pentamethylcyclopentadienyl)(1-phenylnaphthalene-2-yloxy)titanium (IV) (27 mM solution in toluene) (0.4 mL) which had been synthesized from Preparation Example 1 and 10 mM solution of triphenylmethylinium tetrakispentafluorophenylborate (99%, Boulder Scientific) in toluene were sequentially added thereto. By means of ethylene, the pressure in the reactor was then made up to 30 kg/cm$^2$, with continual supply thereof to carry out polymerization. In one minute of the reaction, maximum temperature 172.8° C. was achieved. After 1 minute, 100 mL of ethanol containing 10 vol % of aqueous hydrochloric acid was added to quench the polymerization. Then, the mixture was stirred with 1.5 L of ethanol for 1 hour, and the reaction product was filtered and isolated. The reaction product thus collected was dried in an vacuum oven at 60° C. for 8 hours to obtain 42.0 g of polymer. The polymer had the melting point of 85.3° C., melt index of 17.7 and density of 0.8893 g/cc. As the result of analysis via gel chromatography, the polymer had weight average molecular weight (Mw) of 53,600 g/mol, molecular weight distribution (Mw/Mn) of 2.39, and 1-octene content of 20.7% by weight.

EXAMPLE 2~EXAMPLE 7

In a continuous polymerization device, copolymerization of ethylene with 1-octene was carried out as described below.

As a single activation point catalyst, employed was (dichloro) (pentamethylcyclopentadienyl)(1-phenylnaphthalen-2-yloxy)titanium (IV) (synthesized from Preparation Example 1). The amounts of the catalyst used are shown in Table 1. Ti shows the single activation point catalyst, Al triisobutylaluminum as the cocatalyst, and B triphenylmethylinium tetrakispentafluorophenylborate, respectively. The catalyst was injected after being dissolved in toluene in a concentration of 0.2 g/L. The synthesis was carried out by using 1-octene as the comonomer. Conversion in the reactor can be estimated via reaction condition (when polymerization is carried out for one type of polymer under individual reaction condition) and temperature gradient in the reactor. The molecular weight (for a single activation point catalyst) was controlled as a function of the reactor temperature and 1-octene content. The conditions are shown in Table 1.

TABLE 1

|  | Ex. 2 | Ex. 3 | Ex. 4 | Ex. 5 | Ex. 6 | Ex. 7 |
| --- | --- | --- | --- | --- | --- | --- |
| Flow rate of overall solution (kg/h) | 5 | 5 | 5 | 5 | 5 | 5 |
| Amount of ethylene | 10 | 10 | 10 | 10 | 10 | 10 |
| Proportion of 1-octene (1-octene/ethylene) | 0.3 | 0.3 | 0.3 | 0.3 | 0.3 | 0.3 |
| Amount of Ti (μmol/kg) | 2 | 3 | 4 | 5 | 6 | 7 |
| Al/Ti ratio | 135 | 90 | 68 | 54 | 45 | 39 |
| B/Ti ratio | 3 | 3 | 3 | 3 | 3 | 3 |
| Reaction temperature (° C.) | 151.2 | 151.4 | 151.4 | 152.6 | 149.8 | 151.8 |
| Conversion (%) | 77.3 | 87.9 | 89.5 | 91.0 | 91.4 | 92.7 |
| MI | 1.09 | 4.03 | 5.21 | 5.85 | 6.35 | 7.2 |
| Density | 0.9038 | 0.9016 | 0.9011 | 0.9009 | 0.9006 | 0.9004 |

Ti: Ti in the single activation point catalyst
Al: Triisobutylaluminum as cocatalyst
B: Triphenylmethylinium tetrakispentafluorophenylborate as cocatalyst As can be seen from the Examples, polymers having large weight average molecular weight can be produced under the condition of high temperature (at 140° C. or higher) with low molecular weight distribution, according to the invention. Particularly, one can successfully obtain low-density copolymers from ethylene and 1-octene.

Though the present invention is described in detail with referring to Examples as above, a person having ordinary skill in the art in the field of industry to which the invention belongs can make various modification without departing from the spirit or scope of the invention, which was defined by appended claims. Thus, any alteration or modification of the Examples of the invention to come would not depart from the technique of the present invention.

INDUSTRIAL APPLICABILITY

The transition metal compound according to the invention or the catalyst composition comprising the compound can be easily produced in a simple synthetic procedure with economic advantage. Due to its excellent thermal stability, the catalyst maintains high catalytic activity even at high temperature having high copolymerization reactivity with other olefins to result in polymers with high molecular weight with high yield. Thus, the catalyst has higher commercial practicality than conventional metallocene or non-metallocene type single activation point catalysts already known. Therefore, the transition metal catalyst composition according to the present invention can be usefully employed in preparation of ethylene homopolymers or ethylene copolymer with α-olefin having different physical properties.

The invention claimed is:

1. A transition metal compound represented by Chemical Formula (1):

[Chemical Formula 1]

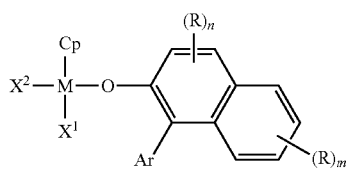

wherein, M represents transition metal from Group 4 in the Periodic Table of Elements;

Cp represents a cyclopentadienyl ring which is $\eta^5$-linkable to M, or a fused ring containing a cyclopentadienyl ring, in which the cyclopentadienyl ring or the fused ring containing a cyclopentadienyl ring is optionally further substituted by (C1-C20)alkyl, (C6-C30)aryl, (C2-C20)alkenyl or (C6-C30)ar(C1-C20)alkyl;

Ar represents (C6-C30)aryl, but Ar is not fluorenyl;

$X^1$ and $X^2$ are independently selected from a group consisting of halogen atoms, (C1-C20)alkyl, (C3-C20)cycloalkyl, (C6-C13)aryl, (C1-C10)alkyl(C6-C13)aryl, (C6-C30)ar(C1-C20)alkyl, (C1-C20)alkoxy, (C3-C20)alkylsiloxy, (C1-C20)alkylamino, (C6-C30)arylamino, (C1-C20)alkylphosphine, (C6-C30)arylphosphine, (C1-C20)alkylmercapto and (C6-C30)arylmercapto;

m is an integer selected from 0 to 4, n is an integer from 0 to 2;

R represents (C1-C10)alkyl, (C3-C10)cycloalkyl, (C6-C13)aryl, (C1-C10)alkyl(C6-C13)aryl, (C6-C13)ar(C1-C10)alkyl or (C1-C10)alkoxy, and the alkyl, cycloalkyl, alkylaryl, aralkyl, alkoxy, alkylsiloxy, alkylamino, arylamino, alkylphosphine, arylphosphine, alkylmercapto, arylmercapto of $X_1$ and $X_2$; the alkyl, cycloalkyl, aryl, alkylaryl, aralkyl, alkoxy of R; and the aryl of Ar are optionally further substituted by one or more substituent(s) selected from a group consisting of (C1-C10)alkyl, (C3-C10)cycloalkyl, (C6-C13)aryl, (C1-C10)alkyl(C6-C13)aryl, (C6-C13)ar(C1-C10)alkyl and (C1-C10)alkoxy, or each of them is optionally linked to an adjacent substituent via (C3-C12)alkylene or (C3-C12)alkenylene with or without a fused ring to form an alicyclic ring, or a monocyclic or polycyclic aromatic ring.

2. The transition metal compound according to claim 1, which is selected from those represented by one of Chemical Formulas (1-1) to (1-3):

[Chemical Formula 1-1]

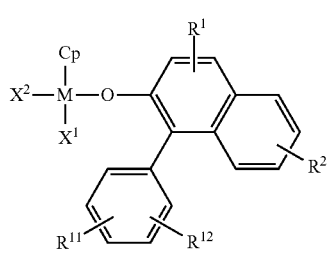

[Chemical Formula 1-2]

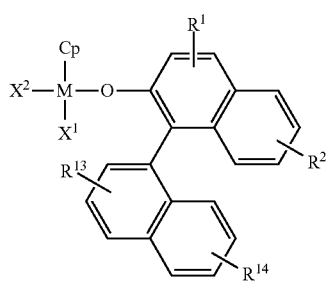

[Chemical Formula 1-3]

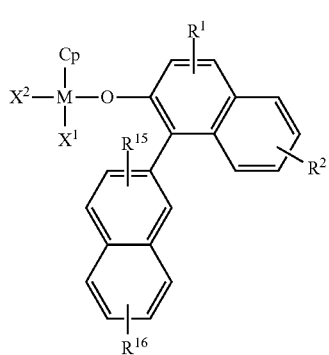

wherein, M is selected from a group consisting of titanium, zirconium and hafnium;

Cp represents cyclopentadienyl or pentamethylcyclopentadienyl;

$X^1$ and $X^2$ are independently selected from a group consisting of chloride, methyl, methoxy, isopropoxy, benzyl and dimethylamino; and $R^1$, $R^2$ and $R^{11}$ through $R^{16}$ are independently selected from a group consisting of hydrogen atom, (C1-C10) alkyl, (C3-C10)cycloalkyl, (C6-C13)aryl, (C1-C10) alkyl(C6-C13)aryl, (C6-C13)aryl(C1-C10)alkyl and (C1-C10)alkoxy.

3. The transition metal compound according to claim 2, which is selected from the following compounds:

1-1-1

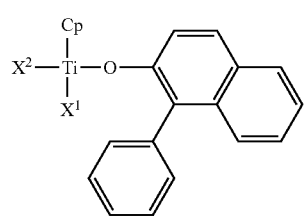

1-1-2

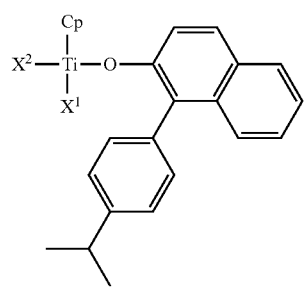

1-1-3

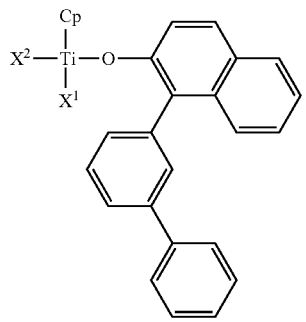

1-2-1

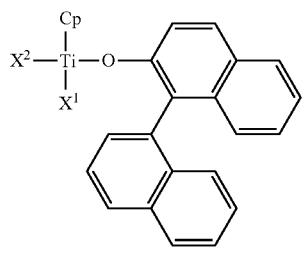

1-2-2

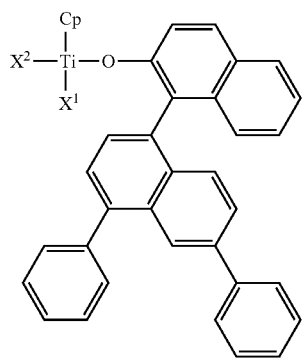

1-3-1

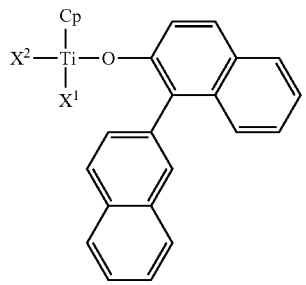

1-3-2

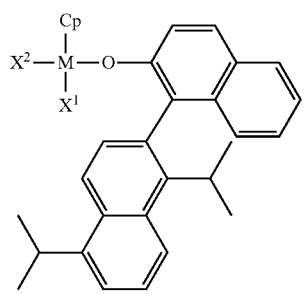

wherein, Cp represents cyclopentadienyl or pentamethylcyclopentadienyl; and $X^1$ and $X^2$ are independently selected from a group consisting of chloride, methyl, methoxy, isopropoxy, benzyl and dimethylamino.

4. A transition metal catalyst composition for preparing ethylene homopolymers or copolymers of ethylene with α-olefin, which comprises a transition metal compound according to claim 1, and alkylaluminoxane or organoaluminum compound cocatalyst, or boron compound cocatalyst, or a mixture thereof.

5. The transition metal catalyst composition for preparing ethylene homopolymers or copolymers of ethylene with α-olefin according to claim 4, wherein the ratio of transition metal to cocatalyst to be used is from 1:50 to 1:5,000 on the basis of the molar ratio of transition metal (M) to aluminum.

6. The transition metal catalyst composition for preparing ethylene homopolymers or copolymers of ethylene with α-olefin according to claim 5, wherein the alkylaluminoxane or organoaluminum compound cocatalyst is selected from methylaluminoxane, modified methylaluminoxane, tetraisobutylaluminoxane, trialkylaluminum, triethylaluminum or triisobutylaluminum, or mixtures thereof.

7. The transition metal catalyst composition for preparing ethylene homopolymers or copolymers of ethylene with α-olefin according to claim 4, wherein the ratio of transition metal to cocatalyst is in the range of 1:0.5~5:10~500 on the basis of the molar ratio of transition metal (M): boron atom : aluminum atom.

8. The transition metal catalyst composition for preparing ethylene homopolymers or copolymers of ethylene with α-olefin according to claim 7, wherein the boron compound cocatalyst is selected from N,N-dimethylanilinium tetrakispentafluorophenylborate or triphenylmethylinium tetrakispentafluorophenylborate, or mixtures thereof.

9. A process for preparing ethylene homopolymers or copolymers of ethylene with α-olefin by using the transition metal catalyst composition according to claim 4, wherein the comonomer to be polymerized with ethylene is one or more compound(s) selected from propylene, 1-butene, 1-pentene, 1-hexene, 1-heptene, 1-octene, 1-decene, 1-undecene, 1-dodecene, 1-tetradecene, 1-hexadecene and 1-eitosene, and ethylene content of the copolymer of ethylene with olefin is from 50 to 99% by weight.

10. The process for preparing ethylene homopolymers or copolymers of ethylene with α-olefin according to claim 9, wherein the pressure in the reactor containing ethylene monomer is from 6 to 150 atm, and the polymerization temperature is from 60 to 250°.

* * * * *